United States Patent [19]

Huygen et al.

[11] Patent Number: 6,116,241
[45] Date of Patent: Sep. 12, 2000

[54] METHOD AND APPARATUS FOR DETERMINING WHEN A PARTIALLY OR COMPLETELY COLLAPSED LUNG HAS BEEN OPENED

[75] Inventors: Paul Huygen, Abcoude, Netherlands; Stephan Böhm, Gladbach; Burkhard Lachmann, Oldenburg, both of Germany

[73] Assignee: Siemens-Elema AB, Solna, Sweden

[21] Appl. No.: 08/889,389

[22] Filed: Jul. 8, 1997

[30] Foreign Application Priority Data

Jul. 8, 1996 [SE] Sweden .................................. 9602699

[51] Int. Cl.$^7$ ................................................. A61M 16/00
[52] U.S. Cl. ................................ 128/204.23; 128/204.21; 128/203.14; 128/205.23; 600/529; 600/671
[58] Field of Search ........................ 128/204.23, 202.22, 128/205.23, 203.14, 204.18, 204.21; 600/529, 532, 533, 538, 586, 483

[56] References Cited

U.S. PATENT DOCUMENTS

| | | |
|---|---|---|
| 4,672,977 | 6/1987 | Kroll ........................................ 600/586 |
| 4,686,999 | 8/1987 | Snyder et al. . | |
| 4,705,048 | 11/1987 | Pfohl ....................................... 600/586 |
| 4,889,130 | 12/1989 | Lee .......................................... 600/483 |
| 4,951,678 | 8/1990 | Joseph et al. ........................... 600/586 |
| 4,981,139 | 1/1991 | Pfohl ....................................... 600/586 |
| 5,165,417 | 11/1992 | Murphy, Jr. . | |
| 5,301,679 | 4/1994 | Taylor ..................................... 600/586 |
| 5,575,283 | 11/1996 | Sjoestrand .......................... 128/204.18 |
| 5,720,709 | 2/1998 | Schnall .............................. 128/204.21 |
| 5,738,090 | 4/1998 | Lachmann et al. ................ 128/203.14 |

FOREIGN PATENT DOCUMENTS 2 129 991 5/1984 United Kingdom .
WO 91/03981 4/1991 WIPO .

*Primary Examiner*—John G. Weiss
*Assistant Examiner*—V. Srivastava
*Attorney, Agent, or Firm*—Hill & Simpson

[57] ABSTRACT

A method and an apparatus for determining when a partially or completely collapsed lung has been opened are based on the fact that in the course of opening an alveolus by supplying a gas pressure, the alveolus will generate a crackle sound. By listening to the crackle sounds via microphones, an apparatus can determine when the lung is completely open. The apparatus has a filter for filtering out the relevant frequencies for the crackle sounds and a determination unit for identifying the crackles and for determining when the lung is open based on the filtered out sounds.

17 Claims, 1 Drawing Sheet

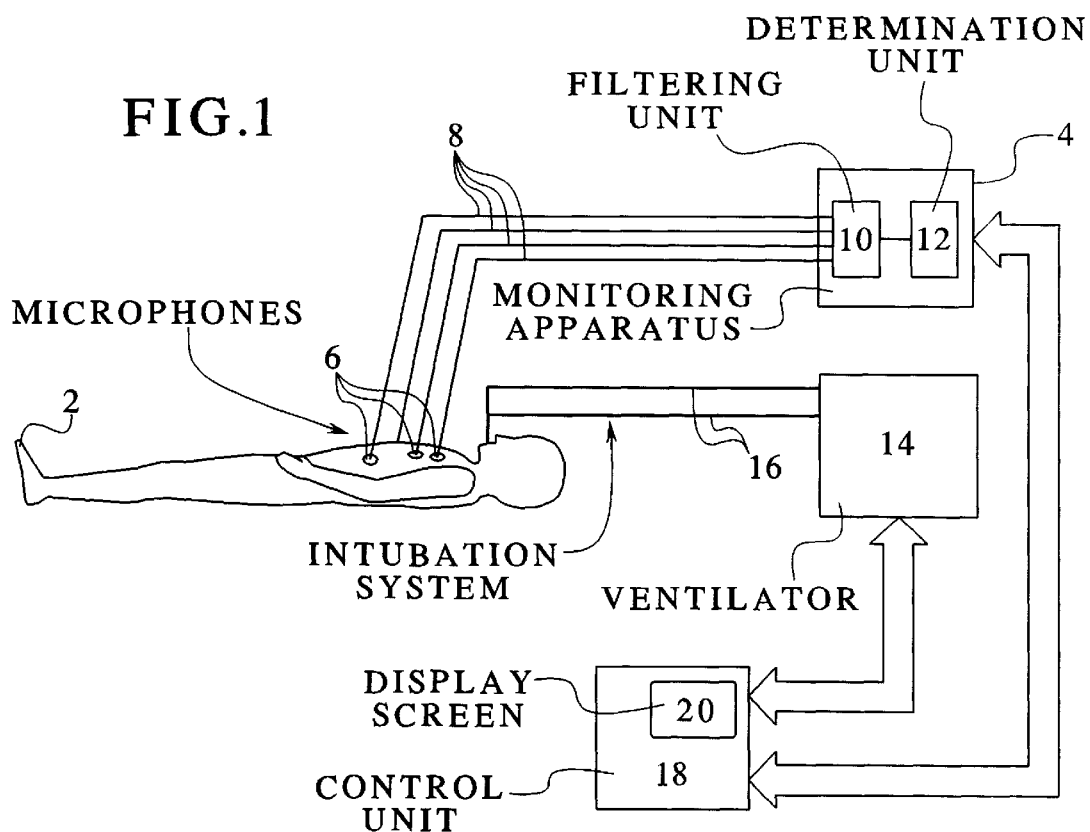
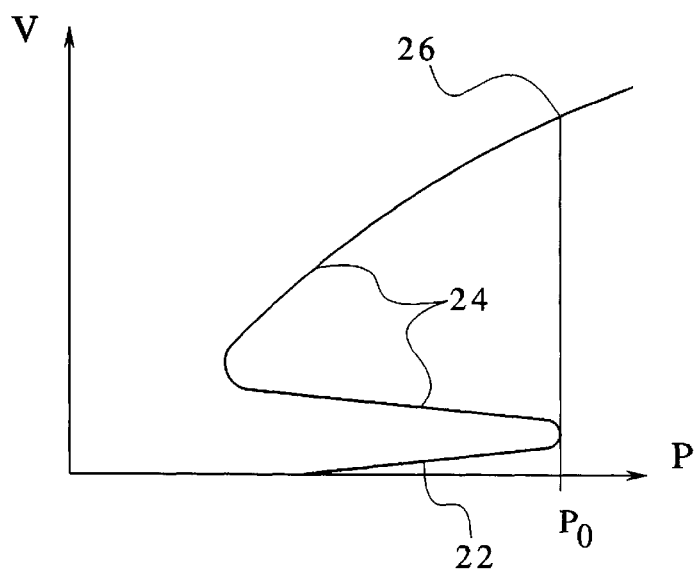

METHOD AND APPARATUS FOR DETERMINING WHEN A PARTIALLY OR COMPLETELY COLLAPSED LUNG HAS BEEN OPENED

BACKGROUND OF THE INVENTION

1. Field of the Invention

The present invention is directed to a method and an apparatus for determining when a partially or completely collapsed lung has been opened and to a use of the apparatus.

2. Description of the Prior Art

In Swedish Application 501 560 corresponding to U.S. Pat. No. 5,575,283, the importance of opening a collapsed lung and keeping it open is described. A ventilator which can calculate an opening pressure for a lung based on measured pressure and volume values is also disclosed. When correlating pressure and volume for a collapsed lung during the opening procedure, an inflection point will normally be present in the curve obtained. This inflection point can be determined mathematically from the obtained curve and represents an opening pressure for the lung.

Determining the inflection point, however, is difficult. The calculated opening pressure will vary depending on the mathematical method used, particularly because the inflection point is not sharp and easy to identify. The reason for this is that the alveoli do not open all at once, but rather in groups forming small clusters or compartments within the lungs. Therefore, the opening of small compartments of alveoli at different pressures will result in several smaller inflection points in the pressure-volume curve. Some of these compartments (or alveoli) can require a higher pressure in order to be opened. When such compartments are present and treatment is given based on the calculated opening pressure, such compartments of the lungs remain closed during the entire respiratory cycle, resulting in an insufficient, or at least impeded, gas exchange for the patient.

The pressure-volume curve analysis described above, therefore, does not indicate when the lung is opened. There is no known apparatus which can determine when the lung is opened or at which pressure the lung is opened.

SUMMARY OF THE INVENTION

An object of the present invention is to provide an apparatus for determining when the lung of a subject is opened in a new and more accurate manner.

Another object of the invention is to provide a method for determining when a partially or completely collapsed lung of a subject has been opened.

Yet another object of the invention is to achieve the use of an apparatus for determining an opening pressure in combination with a ventilator. In particular, a ventilator incorporating such an apparatus.

The above objects are achieved in accordance with the invention in a method and an apparatus wherein an audio recording of sounds emanating from the lung region of a subject is obtained, the distinctive sounds relating to opening of alveoli are filtered out of the audio signal, and a determination as to when the lung is sufficiently opened is made based on the filtered out portion of the audio signal.

A closed alveolus is very stiff. When a gas is supplied to the alveolus at a steadily increasing pressure, the pressure must be increased up to a certain threshold, which is specific, for each alveolus. Then the alveolus starts to open. As the alveolus opens, the compliance will increase rapidly and the alveolus fills with gas until a steady state is reached. The steady state will be at the same pressure as when the alveolus started to open (if gas is supplied—otherwise the pressure will have decreased), but the alveolus will now contain a specific volume of gas. During the rapid increase in the compliance, as the alveolus opens, a crackle sound is generated. This crackle sound is very specific for the alveoli as they open. By recording, measuring or in any manner picking up the sounds from the lung, these crackles can be filtered out and identified by a suitable calculation unit, such as a computer or similar device. When the crackle sounds have ebbed away, the lung is open and the supplied pressure corresponds to the opening pressure.

More specifically, a more correct opening pressure can be determined by applying a suitable pressure ramp for the gas supplied to the lungs and to register both pressure and crackle sounds (similar to when forming a pressure-volume diagram). Since the crackle sounds are much more definite than volume changes as to both presence and source, it is much easier to read out the opening pressure from a correlated pressure-sound recording.

Lung sound detection systems are known in general, as disclosed, for example, in European Application 491 781. These systems, however, are generally directed to picking up lung sounds which arise due to a pathology or abnormality for diagnosing different lung diseases and therefore this document does not recognize or suggest the possibility of determining when a collapsed lung has been opened up.

In an embodiment of the invention wherein multiple microphones respectively disposed at different locations around the lung region, the location of the crackle sounds and information regarding which compartments that are being opened can also be determined.

Basically the method performs the same steps which the apparatus can carry out, i.e., picking up or listening to sounds from the lung region, filtering out sound related to the opening of alveoli and determining when the lung is sufficiently open based on the filtered out sound.

In an embodiment of the method sounds are measured from several parts of the lung region and the compartments of the lung that generate the sound are identified.

It is particularly advantageous to use the inventive apparatus in combination with a ventilator, with the supply of respiratory gas from the ventilator to the lung can being controlled based on, inter alia, the determination of the supplied pressure at which the lung is opened.

The use can be improved by determining when different compartments of the lung open. When used over a number of consecutive respiratory cycles, the combined use of the apparatus and the ventilator can be utilized to determine which parts of the lung close during each respiratory cycle. This is of particular importance when the lungs only collapse partially at the end of each respiratory cycle. It is, in a similar manner, also possible to determine a lowest acceptable pressure at which the lungs are sufficiently open during the entire respiratory cycle.

It is in this case also an advantage to incorporate the apparatus according to the invention completely into a ventilator.

DESCRIPTION OF THE DRAWINGS

FIG. 1 shows a patient connected to an apparatus, constructed and operating according to the invention, and to a ventilator.

FIG. 2 shows a pressure-volume curve for an alveolus for use in explaining the inventive apparatus and method.

DESCRIPTION OF THE PREFERRED EMBODIMENTS

FIG. 1 shows a patient 2 connected to a monitoring apparatus 4 which determines when the lungs of the patient 2 have opened. A number of microphones 6 are attached at the chest wall on the patient 2 for picking up sound from this region of the patient 2. The microphones 6 are connected to the monitoring apparatus 4 via signal lines 8. The microphones 6 can be connected via a small air space, approximately 5–15 ml of volume, to the chest wall. This air space provides an air coupling to the chest wall.

The monitoring apparatus 4 includes a filtering unit 10 and a determination unit 12. The filtering unit 10 filters out sound which is related to the crackle sound which occurs when an alveolus or several alveoli open. The filtering unit 10 can include e.g. a third order Butterworth high pass filter with a cut off frequency of 50 Hz, or any other suitable filter.

The determination unit 12 be devised as an analog or digital unit. The determination can be carried out by software or hardware within the determination unit 12. When using digital systems, the filtered signal can be amplified and digitized using a sampling frequency of, for instance, 20 kHz. A suitable algorithm for detecting the crackles is also implemented in the determination unit 12. For instance, Fourier analysis can be applied. The crackle sounds are known per se, and algorithms exist which selectively can identify the corresponding signals.

Also connected to the patient 2 is a ventilator 14. The ventilator 14 includes an intubation system 16 for supplying respiratory gas to and removing respiratory gas from the patient 2. Both the monitoring apparatus 4 and the ventilator 14 are connected to a control unit 18, which has a screen 20 for displaying information about the treatment and condition of the patient 2, as well as the measurements made on the patient 2. Via the control unit 18, the ventilator 14 can be controlled based on, inter ala, the analysis of the lung sounds made by the monitoring apparatus 4.

In FIG. 2 a pressure-volume curve of an individual alveolus is shown. As a pressure is supplied to the alveolus, as shown in the first part 22 of the curve, pressure will increase relatively rapidly while only a very small volume of gas enters the alveolus.

As the supplied pressure reaches a certain pressure—the opening pressure $P_O$—a rapid change occurs, indicated by a second part 24 of the curve. The pressure will drop significantly as the compliance of the alveolus rapidly increases and gas will flow into the alveolus. Subsequently both the pressure and the volume increase until, at point 26, an equilibrium between the pressure in the alveolus and the supplied pressure has been reached.

If a further pressure is supplied at this stage, the volume will increase in a more or less linear fashion until the limit of expansion for the alveolus is reached. At that point, the pressure will again increase rapidly in relation to the volume increase. Such pressures should be avoided, however, since they not only can damage the alveolus and rupture the tissue, but also can compress the important capillaries near the alveolus and impede the gas exchange.

The determination of when the lung should be considered open can be made by awaiting the complete ebbing away of crackle sounds. Such an approach can be particularly useful when the lung is only partially collapsed but otherwise in a fairly good condition.

As an alternative, crackles from different compartments of the lung can be identified and used as an indication of when a sufficient number of important compartments have opened. This is then a marker for when the lung is sufficiently open.

Another way of utilizing the crackle sound for determining when the lung is open is to set a threshold, either for a frequency or a number of crackles, to be reached.

Yet another way of utilizing the sound, is for determining the opening pressure in a more accurate manner. For instance, gas exhibiting a pressure ramp is supplied to the partially collapsed lung and pressure and sounds are registered (similar to obtaining a pressure-volume or pressure-flow diagram). Based on the registrations, which can be made for one or several respiratory cycles, the pressure at which substantially all alveoli have opened can be determined. The crackle sounds are distinct and are only related to alveoli which are opened. The correlating opening pressure is therefore much easier to determine than when using volume changes, which depend more on the volume change in the opened alveoli than on the actual opening of alveoli—at least for the partially collapsed lung.

The determined opening pressure can then be used for setting an appropriate peak inspiratory pressure, PIP, which will ensure that the lungs open sufficiently during each respiratory cycle. The treatment can thus be optimized so that the pressure supplied to the lungs (PIP) can be minimized while obtaining a non-impeded gas exchange in the lungs.

The monitoring apparatus 4 can also be used for controlling the ventilator 14 in other ways. For instance the end pressure of respiratory gas supplied by the ventilator (PEEP) may be increased over a consecutive number of respiratory cycles, until the monitoring apparatus 4 no longer detects any crackle sounds. In other words, until the lung is completely open during the entire respiratory cycle. The lowest pressure at which the lung remains open at all times thus can be determined by means of the monitoring apparatus 4 and used in the control of the ventilator 14 as a set value for PEEP.

The monitoring apparatus 4 can also be used in a reverse manner for controlling the ventilator 14. For this purpose, the supplied end pressure respiratory gas can be decreased in small steps over a number of respiratory cycles (maintaining a sufficiently high peak pressure for all cycles) and when crackles begin to appear during inspiration phases it can be established that some alveoli collapse at the end of the respiratory cycle. By allowing a certain amount of alveoli in non-dependent compartments to collapse, a lower end pressure can be supplied. This systematic lowering of the pressure can also be used as the lung recovers and more alveoli remain open at lower pressures. The upper pressure can normally also be decreased in these cases.

Since crackles normally begin in the zone between the dependent and the nondependent parts of the lungs, the determination of where the alveoli open is important. By registering when alveoli in the important dependent parts of the lungs have started to open, a different threshold can be set for determining when the lung is open.

It is possible to use the monitoring apparatus 4 as a completely separate unit for determining when the lung has been opened, i.e., without the control unit 18. The apparatus can also be completely integrated with the ventilator 14 (forming a new advanced ventilator) or with any other device intended for opening up partially or completely collapsed lungs.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for determining when an at least partially collapsed lung of a subject has been opened by gas pressure supplied to the lung from a ventilator comprising:

means for obtaining an audio signal from a lung region of a subject, said audio signal including a distinctive component produced by opening of alveoli in the lung;

filtering means for filtering out said distinctive component; and evaluation means supplied with said distinctive component filtered out of said audio signal for determining, from said distinctive component, a degree of opening of the lung.

2. An apparatus as claimed in claim 1 wherein said means for obtaining said audio signal comprises a plurality of microphones adapted for attachment to said subject, and wherein said evaluation means comprises means for determining a location of alveoli which have been opened.

3. An apparatus as claimed in claim 2 wherein said evaluation means comprises means for determining that said lung is opened when alveoli in predetermined locations in said lung are opened.

4. An apparatus as claimed in claim 1 wherein said evaluation means comprises means for determining that the lung is opened when said distinctive component reaches a predetermined threshold.

5. An apparatus as claimed in claim 4 wherein said predetermined threshold comprises a frequency threshold.

6. An apparatus as claimed in claim 4 wherein said predetermined threshold comprises a predetermined number of distinctive components.

7. An apparatus for ventilating a subject comprising:

ventilator means for supplying respiratory gas to the lungs of a subject;

means for obtaining an audio signal from a lung region of a subject, said audio signal including a distinctive component produced by opening of alveoli in the lung;

filtering means for filtering out said distinctive component;

evaluation means supplied with said distinctive component filtered out of said audio signal for determining, from said distinctive component, a degree of opening of the lung; and control means for controlling supply of said respiratory gas from said ventilator dependent on the degree to which the lung is opened.

8. An apparatus as claimed in claim 7 wherein said means for obtaining said audio signal comprises a plurality of microphones adapted for attachment to said subject, and wherein said evaluation means comprises means for determining a location of alveoli which have been opened.

9. An apparatus as claimed in claim 8 wherein said evaluation means comprises means for determining that said lung is opened when alveoli in predetermined locations in said lung are opened.

10. An apparatus as claimed in claim 7 wherein said evaluation means comprises means for determining that the lung is opened when said distinctive component reaches a predetermined threshold.

11. An apparatus as claimed in claim 10 wherein said predetermined threshold comprises a frequency threshold.

12. An apparatus as claimed in claim 10 wherein said predetermined threshold comprises a predetermined number of distinctive components.

13. An apparatus as claimed in claim 7 wherein said control means comprises means for controlling supply of said respiratory gas by increasing a gas pressure of said respiratory gas until a predetermined distinctive component occurs in said audio signal.

14. An apparatus as claimed in claim 7 wherein said control means comprises means for determining a lowest gas pressure which maintains the lungs open during an entire respiratory cycle by controlling delivery of said respiratory gas for producing a sequence of respiratory cycles with respectively varying PEEP and correlating each PEEP with the distinctive component obtained during that respiratory cycle.

15. A method for determining whether an at least partially collapsed lung of a subject has been opened by gas pressure supplied to the lung, comprising the steps of:

recording an audio signal from a lung region of a subject, said audio signal including distinctive components produced by opening of alveoli in the lung;

filtering out said distinctive components from said audio signal; and determining a degree of opening of the lung dependent on the distinctive components filtered out of said audio signal.

16. A method as claimed in claim 15 wherein the step of obtaining said audio signal comprises obtaining a plurality of audio signals from different locations in said lung region, and wherein the step of determining a degree to which the lung is opened comprises determining from which of said locations each distinctive component emanated, and determining that the lung is opened when a predetermined region of said lung has opened.

17. A method for ventilating a subject comprising:

supplying respiratory gas to an at least partially collapsed lung of a subject;

recording an audio signal from a lung region of a subject, said audio signal including distinctive components produced by opening of alveoli in the lung;

filtering out said distinctive components from said audio signal;

determining a degree of opening of the lung dependent on the distinctive components filtered out of said audio signal; and controlling the supply of said respiratory gas dependent on the degree to which said lung is opened based on said distinctive components.

* * * * *